(12) United States Patent
Lapidus et al.

(10) Patent No.: US 6,331,574 B1
(45) Date of Patent: Dec. 18, 2001

(54) PROCESS FOR THE PREPARATION OF HIGH ACTIVITY CARBON MONOXIDE HYDROGENATION CATALYSTS; THE CATALYST COMPOSITIONS, USE OF THE CATALYSTS FOR CONDUCTING SUCH REACTIONS, AND THE PRODUCTS OF SUCH REACTIONS

(75) Inventors: Albert L'Vovoch Lapidus, Kashirskoje Shosse; Alla Jurievna Krylova, Graivorovskaja Ulitsa, both of (RU); Michel A. Daage; Russell J. Koveal, both of Baton Rouge, LA (US); Rocco A. Fiato, Basking Ridge, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/415,084

(22) Filed: Oct. 8, 1999

(51) Int. Cl.$^7$ ............... C07C 27/00; C07C 5/13; B01J 20/34
(52) U.S. Cl. ............... 518/709; 518/700; 502/20; 585/734
(58) Field of Search ............... 518/700, 709; 502/20; 585/734

(56) References Cited

U.S. PATENT DOCUMENTS

| | | | |
|---|---|---|---|
| 4,148,750 | 4/1979 | Pine | 252/416 |
| 4,255,349 | 3/1981 | Butter et al. | 260/449.6 R |
| 4,280,897 | 7/1981 | Shah et al. | 208/113 |
| 4,394,355 | 7/1983 | Frugé | 423/27 |
| 4,677,085 | 6/1987 | Nevitt | 502/26 |
| 5,811,469 * | 9/1998 | Leviness et al. | 518/700 |

FOREIGN PATENT DOCUMENTS

WO 95/31280   11/1995   (WO) ............... B01J/21/04
WO 98/57743   12/1998   (WO) ............... B01J/29/00

OTHER PUBLICATIONS

Kazutaka et al, Appl. Surf. Sci. (1997), 121/122, 433–436.*

* cited by examiner

Primary Examiner—Sreeni Padmanabhan
Assistant Examiner—J. Parsa
(74) Attorney, Agent, or Firm—Jay Simon; Charles J. Brumlik

(57) ABSTRACT

A process for the preparation of a catalyst useful for conducting carbon monoxide hydrogenation reactions, especially Fischer-Tropsch reactions. The steps of the process begin with the activation, or reactivation, of a deactivated catalyst, or with the preparation and activation of a fresh catalyst. In accordance with the latter, the steps of the process comprise, first contacting, in one or more steps, a powder or preformed, particulate refractory inorganic support with a liquid, or solution in which there is dispersed or dissolved a compound, or salt of a catalytically active metal, or metals, to impregnate and deposit the metal, or metals, upon the support, or powder. The metal, or metals, impregnated support is calcined following each impregnation step to form oxides of the deposited metal, or metals. The calcined catalyst precursor is then treated with a solution of a chelating compound, preferably a poly- or multidentate chelating compound, sufficient to complex with, extract and remove a portion of the oxides of the metal, or metals. The catalyst is activated by reduction; suitably by contact with hydrogen. In the activation, or reactivation of a deactivated catalyst, the catalyst is first treated with the chelating compound to extract a portion of the oxides of the metal, or metals, and the catalyst is then reduced. In either event, the activated or reactivated catalyst has high activity, or high $C_5+$ selectivity, or both high activity and $C_5+$ selectivity in conducting carbon monoxide hydrogenation reactions. The productivity of the process is increased.

11 Claims, No Drawings

//PROCESS FOR THE PREPARATION OF HIGH ACTIVITY CARBON MONOXIDE HYDROGENATION CATALYSTS; THE CATALYST COMPOSITIONS, USE OF THE CATALYSTS FOR CONDUCTING SUCH REACTIONS, AND THE PRODUCTS OF SUCH REACTIONS

1. FIELD OF THE INVENTION

This invention relates to a process for the preparation of novel, highly active catalysts for conducting carbon monoxide hydrogenation reactions, especially Fischer-Tropsch reactions. It also relates to the catalyst, to the process utilizing the catalyst, and to the product of such process; particularly transportation fuels and lubricating oils derived from synthesis gas.

2. BACKGROUND

The improvement of Fischer-Tropsch (F-T) catalysts, i.e., catalysts useful for the production of petrochemicals and liquid transportation fuels by hydrogenation of carbon monoxide, has been the subject of ongoing research for some years; and this work continues. Early commercial work with the F-T process began in Germany in the 1920's, and was continued, resulting in the SASOL plants of South Africa. F-T synthesis is well documented in the technical and patent literature. The Group VIII metals, e.g., ruthenium and the Iron Group Metals such as iron and cobalt, have been used extensively as catalytic metals in the production of F-T catalysts, and these metals have been promoted or modified with various other metals, and supported on various substrates in formation of the catalysts.

Cobalt catalysts, particularly the promoted cobalt catalysts, e.g., those constituted of cobalt and rhenium, or cobalt, thoria and rhenium, supported on titania, or other titania-containing support have been found to exhibit high selectivity in the conversion of methanol to hydrocarbon liquids, or synthesis of hydrocarbon liquids from hydrogen and carbon monoxide as disclosed, e.g., in U.S. Pat. No. 4,568,663. The catalysts can be prepared by gellation or cogellation techniques, but typically they are prepared by deposition of the metal, or metals, on the previously pilled, pelleted, beaded, extruded, or sieved support material, or a powder by the impregnation method. In preparing the composite catalysts, the metals are deposited from solution on the support in preselected amounts to provide the desired absolute amounts and weight ratio of the respective metals, e.g., cobalt and rhenium. Suitably, e.g., the cobalt and rhenium are composited with the support by contacting the support with a solution of a cobalt-containing compound, or salt, or a rhenium-containing compound, or salt, e.g., a nitrate, carbonate or the like. Optionally, cobalt and rhenium can be co-impregnated upon the support. The cobalt and rhenium compounds used in the impregnation can be any organometallic or inorganic compounds which decompose to give cobalt and rhenium oxides upon calcination, such as a cobalt, or rhenium nitrate, acetate, acetylacetonate, naphthenate, carbonyl, or the like. The amount of impregnation solution used should be sufficient to impregnate the catalyst via the incipient wetness technique, or sufficient to completely immerse the carrier, usually a volume of liquid ranging from about 1 to 20 times of the carrier by volume, depending on the metal, or metals, concentration in the impregnation solution. The impregnation treatment can be carried out under a wide range of conditions including ambient or elevated temperatures. The catalyst, after impregnation, is dried, and calcined; suitably by contact with oxygen, air or other oxygen-containing gas at temperature sufficient to oxidize the metal, or metals; e.g., to convert cobalt to $Co_3O_4$. The catalyst, or catalyst precursor, is then reduced and activated by contact of the oxidized metal, or metals, with hydrogen, or hydrogen-containing gas.

The reduced catalysts, e.g., cobalt catalyst, and cobalt catalyst promoted with other metals, have been found to provide relatively high selectivity, activity and activity maintenance in methanol conversion, and in the conversion of hydrogen and carbon monoxide to distillate fuels; predominantly $C_5+$ linear paraffins and olefins, with low concentrations of oxygenates. Nonetheless, there remains a pressing need for F-T catalysts of yet higher activity; particularly more active catalysts capable of producing transportation fuels and lubricants of high quality at good selectivity and high levels of productivity.

3. THE INVENTION

This need and others are achieved in accordance with the present invention which embodies the activation, or reactivation of a deactivated catalyst, or the preparation and activation of a fresh catalyst. The process requires, in the preparation of the catalyst, contacting a powder or preformed particulate solids support, suitably a refractory inorganic oxide support, preferably a crystalline aluminosilicate zeolite, natural or synthetic, alumina, silica, silica-alumina or titania in one or a series of two or more steps with a liquid, or solution, suitably an aqueous solution containing a compound, or salt of a catalytic metal, or metals, preferably a Group VIIB or Group VIII metal, or metals, of the Periodic Table of the Elements (Sargent-Welch Scientific Company; Copyright 1968) to impregnate and deposit the metal, or metals, upon the powder or support. The impregnated powder or support is then calcined. Generally, two to four or more metal impregnations, with intermediate calcination of the metal, or metals, impregnated support is preferred, and is sufficient to deposit from about 5 percent to about 70 percent, preferably from about 10 percent to about 30 percent metallic metal, or metals, upon the support or powder, based upon the total weight (wt. %) of the calcined catalyst.

An inactive or deactivated catalyst, or the calcined catalyst, or catalyst precursor, is then contacted, and treated with a solution of a chelating compound, preferably a poly- or multidentate chelating compound, sufficient to complex with, extract and remove some of the metal atoms present in the oxides, or reduced metal particles, and increase the activity or $C_5$ + selectivity, or both the activity and $C_5+$ selectivity of the catalyst in its use, after reduction, in the hydrogenation of carbon monoxide, or conduct of Fischer-Tropsch synthesis reactions. The extraction, and removal of some of the catalytic metal from the catalyst, or calcined catalyst precursor, in this manner to increase the activity of the catalyst is indeed a surprising effect since past experience has shown that the activity of a catalyst constituted of a given metal, e.g., cobalt, is directly related to the amount of metallic metal, e.g., metallic cobalt, contained on the catalyst; the greater the amount of metallic cobalt contained on the catalyst, after reduction, the greater the activity of the catalyst in conducting carbon monoxide hydrogenation reactions, especially in converting synthesis gas, or mixtures of hydrogen and carbon monoxide, to $C_5+$ hydrocarbons. However, it is found that treatment of a deactivated, or calcined metal, or metals, loaded catalyst or catalyst precursor, with the chelating compound sufficient to extract, or remove the metal, or metals, to leave from about 1 percent to about 80 percent, preferably from about 25 percent to about 75 percent, of the metal, or metals present before the extraction, measured as metallic metal, will increase the activity of the catalyst, after reduction, as much as about 10 percent, and higher, and often as much as 25 percent; activity values considerably in excess of those which can be achieved by reducing the deactivated or calcined catalysts without first treating the deactivated, or calcined catalysts with the chelating compound. Moreover, the $C_5+$ selectivity of the catalyst is increased, resulting in as much as a four-fold increase in productivity.

In impregnating the support to form a catalyst, it is believed that the metal, e.g., cobalt, initially deposits within the pores of the support, and is then laid down along the peripheral surface between the pores, bridging over and covering some of the previously open pores, or pore mouths. On calcination the cobalt is converted to $Co_3O_4$. Reduction of the cobalt oxide component e.g., with hydrogen, as in conventional practice produces a catalyst active for the hydrogenation of carbon monoxide, or conversion of a synthesis gas to $C_5+$ hydrocarbons. On the other hand however, if before reducing the catalyst with hydrogen, the same catalyst, or catalyst precursor is contacted, and treated by extraction with the chelating compound, e.g., sodium ethylene diamine tetraacetic acid, a portion of the $Co_3O_4$ deposits are removed from the pores to form a catalyst which, on reduction, albeit it contains a lesser amount of cobalt, is considerably more active for the hydrogenation of carbon monoxide, or conversion of a synthesis gas to $C_5+$ hydrocarbons, than the more highly metal loaded catalyst, or catalyst precursor not so treated with the chelating compound. In other words, the activity, or $C_5+$ selectivity, or both the activity and $C_5+$ selectivity, is higher than that of the more highly metal loaded catalyst, or catalyst precursor not so treated with the chelating compound.

An inactive catalyst, or catalyst deactivated in having been previously used in a carbon monoxide hydrogenation operation, or freshly prepared support with which a metal, or metals, has been composited, in the practice of this invention, is thus treated as follows: It is contacted, and leached with a liquid, or solution containing any of a variety of chelating compounds, preferred of which are poly- or multidentate chelating compounds. Poly- or multidentate chelating compounds suitable for the practice of this invention are characterized as having a denticity of two or more, preferably six, functional coordinating groups or ligands which form chelated metal cations with the oxidized catalytic metal, or metals, of the catalyst or catalyst precursor. The poly- or multidentate chelating compound, or compounds, is dispersed, or dissolved in the liquid medium, suitably an aqueous medium, in concentration sufficient to complex with, dissolve and remove chelated metal cations of the catalytic metal, or metals, from the pores of the support. On reduction, e.g., by contact with hydrogen, the activity of the catalyst contacted and treated with the chelating compound will be greater than a catalyst otherwise similar except that it has not been treated with the chelating compound, or compounds, albeit lower in content of total metallic metal. Whereas the reason for this increased activity is not fully understood, it is believed that better diffusion through the pores is obtained by treatment of the catalyst or catalyst precursor with the chelating compound. Moreover, the surface area of the metallic crystallites may be increased by the treatment.

4. DETAILED DESCRIPTION

Further details describing the preparation and activation of a fresh catalyst, and the activation, or reactivation, of an inactive or deactivated catalyst is given as follows: First, in the preparation of a fresh catalyst, the precursor catalyst composite is prepared by (1) initially contacting a powder or preformed particulate solids support, suitably but not limited to carbides, nitrides, alumina and zirconia, but particularly a refractory inorganic oxide support, preferably silica or silica-alumina, and more preferably titania, and including crystalline aluminosilicates or zeolites, natural and synthetic, particularly those of large pore size ranging up to about 100 Angstrom Units (Å), this including A zeolite, X zeolite, Y zeolite, mordenite, ZSM-zeolite, silicalites, MCM, ALPO, SAPO and the like, with a liquid, or solution, containing a compound, or salt of a catalytic metal, or metals, suitably a Group IIIB, IVB, VB, VIB, VIIB or VIII metal, or metal of the lanthanum or actinium series, preferably a Group VIIB or VIII metal, especially an Iron Group metal, i.e., a compound, or salt of iron, cobalt, nickel, or mixture thereof, in one, or in a series of steps: preferably two to four steps. Compounds suitable as sources of the Iron Group metal are, e.g., cobalt nitrate, cobaltous hydroxyquinone, cobalt acetate, cobalt carbonyls, iron acetate, nickel acetate, nickel acetylacetonate, nickel naphthenate, and the like. Suitably, a promoter metal is similarly added, serially or simultaneously from a solution containing a salt or compound of the metal, e.g., ruthenium or rhenium, to promote, or modify the activity, or selectivity, of a given catalyst for conducting a carbon monoxide hydrogenation, or F-T reaction. For example, although an Iron Group metal/titania catalyst is highly active for the conversion of synthesis gas, or highly selective for the production of $C_5+$ hydrocarbons, or both, an additional metal, or metals, can be included as a promoter, or modifier if desired. Ruthenium or other Group VIII noble metal, rhenium or the like may thus be included, the amount thereof ranging up to a 1:12 ratio of promoter metal:Iron Group metal (wt. basis), preferably up to a 1:80 ratio of promoter metal to Iron Group metal (wt. basis). Thus, a Ru:Co ratio of about 1:80 and a Re:Co ratio of about 1:12 provides highly active catalysts. In general, it is preferred to codeposit the promoter metal, or metals, onto the support simultaneously with the catalytic metal, or metals, e.g., rhenium and an Iron Group metal, or metals. This can be done, e.g., by using a compound, or salt of the promoter metal, or metals, added with a compound, or salt of the catalytic metal, or metals, dissolved in the same solvent; or the promoter metal, or metals, may be deposited after deposition of the Iron Group metal, or metals, by dissolving a compound, or salt of the promoter metal, or metals, in a different solution and impregnating the preformed Iron Group metal/silica catalyst composite. Water is the preferred dispersing agent, or solvent, but a wide variety of organic, or hydrocarbons, may also be suitable as dispersing agents, or solvents for dispersing or dissolving the salt of the Iron Group metal, or metals, and added promoter metal, or metals. Exemplary of selectively useful solvents are straight chain, branched chain or cyclic aliphatic hydrocarbons, saturated or unsaturated, substituted or unsubstituted, such as hexane, cyclohexane, methyl cyclohexane, and the like; aromatic hydrocarbons substituted or unsubstituted, such as benzene, toluene, xylenes, ethylbenzene, cumene, and the like. If desired, the impregnated support may be dried. The drying step, if employed, is conducted at temperature ranging preferably from about ambient to about 120° C. The drying step is conducted at pressures below atmospheric, above atmospheric, or at atmospheric or ambient pressure.

The metal, or metals, e.g., iron, cobalt or nickel, can be loaded upon a solids support component, e.g., a catalyst formed by compositing the metal, or metals, with titania, or a zeolite, in concentrations ranging from about 5 percent to about 70 percent, and greater, preferably from about 10 percent to about 30 percent, measured as elemental metal, based on the total weight of the catalyst [wt. %; dry basis]. The metal, or metals, can be loaded upon, and effectively extracted pursuant to the practice of this invention from powders or solids supports having a wide range of pore sizes, but has been found particularly effective in treating supports of average pore radius below about 100 Å. A preferred property of the support is that it have an average pore radius ranging between about 15 Å and 40 Å, more preferably from about 20 Å to about 35 Å. Typically, the metal, or metals, is composited with the support by impregnation of the support up to or beyond the point of incipient wetness.

(2) The metal, or metals, impregnated support is then calcined, and the metal, or metals, component thereof oxidized and the metal, or metals converted to an oxide by heating in an oxidizing atmosphere at temperatures ranging from about 100° C. to about 700° C., preferably from about 150° C. to about 450° C.

(3) Optionally, and preferably, steps (1) and (2), supra, are repeated in seriatim, and this sequence of treatments can be repeated one or more additional times, generally from about 2 to about 4 or more times, until the desired amount of the metal, or metals, has been loaded onto the catalyst.

An inactive or deactivated catalyst, e.g., such as one removed from an operating F-T reactor unit, or the precursor catalyst from Step (2) or Step (3), or support containing the metal, or metals, oxide component is (4) activated by contact, and treatment with a solution of a chelating compound, suitably a poly- or multidentate chelating compound, or compounds, sufficient to complex with, extract and remove some of the metal oxide(s) to activate, or increase the activity, or $C_5+$ selectivity, or both the activity and $C_5+$ selectivity of the catalyst when reduced and used in the hydrogenation of carbon monoxide, or conduct of F-T reactions. Exemplary of chelating compounds suitable for this purpose are nitrogen, or oxygen, or nitrogen and oxygen containing compounds which contain chelating ligands (i.e., functional coordinating groups which have one or more pairs of electrons available for the formation of coordinate bonds), preferably those having a denticity of at least two, and more preferably six or more. The solvent for the chelating compound is one which has the capacity to dissolve, or solubilize both the chelating agent and the metal complex formed during the extraction. Molten wax and water are preferred solvents, but hydrocarbon solvents can be used. The chelated metal compound chelates with the metal atoms present in the oxides, or reduced metal particles, becomes solubilized in the solution, and is extracted by the solution and removed from the support.

The preferred chelating metal compound that is used for the extraction of a metal, e.g., cobalt, must thus include at least one polydentate ligand, and preferably the total denticity of the polydentate ligand, or compound, will be at least two, and preferably range from about two to six. Thus, e.g., where the denticity of a compound is six, it may contain one monodentate ligand and another ligand having a denticity of five; three bidentate ligands; a bidentate and a quadridentate ligand; or two tridentate ligands. Preferred compounds contain three bidentate or two tridentate ligands, particularly the latter. Typical ligands for extraction of catalytic metals are, e.g., carboxylic acids, ketones, aldehydes, alcohols, ethers, and esters having oxygen and amine or nitrogen-containing heterocycles. For example, the following exemplifies common multidentate ligands useful for the extraction of cobalt ions, to wit: ethylene diamines, alkyl diamines, diethylenetriamines, dialkyltriamines, acetylacetone, alkyl dicarboxylic acids and alkali salts of carboxylic acids. Exemplary of preferred poly- or multidentate compounds suitable for this purpose are the ammonium and alkali salts of compounds having the formula:

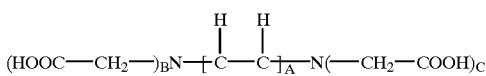

wherein
A is an integer ranging from 1 to about 6, preferably 1; B and C are integers defining the number of carboxyl groups associated with N,
B being an integer ranging from 0 to 2, and
C an integer ranging from 0 to 2;
with the sum of
B and C ranging from 2 to 4, preferably 4.

Exemplary of such multidentate chelating compounds are ethylene diamine diacetic acid, ethylene diamine tetraacetic acid, diethylene diamine diacetic acid, tetraethylene diamine diacetic acid and tetraethylene diamine tetraacetic acid. Of such compounds, ethylene diamine tetraacetic acid is preferred.

The poly- or multidentate liganous compound, or compounds, e.g., an ammonium or alkali containing salt (a salt of $NH_4$, Na, K, Li or the like) is dispersed, or dissolved in a liquid in concentration ranging from about 0.001 percent to about 20 percent, preferably from about 0.01 percent to about 10 percent, based on the total weight of the chelating compound, or compounds, and the liquid; preferably molten wax or water, though generally any liquid in which both the chelating agent and the extracted metal complex will solubilize is adequate as a solvent.

(5) The catalyst, or catalyst precursor, after extraction with the chelating agent is reduced; suitably by contact with hydrogen or a hydrogen-containing gas, thus activating the catalyst.

Hydrocarbon Synthesis

In conducting the preferred Fischer-Tropsch, or F-T synthesis reaction, a mixture of hydrogen and carbon monoxide is reacted over an Iron Group metal catalyst, e.g., a cobalt or ruthenium catalyst, to produce a waxy product which can be separated in various fractions, suitably a heavy or high boiling fraction and a lighter or low boiling fraction, nominally a 700° F.+ (372° C.+) reactor wax and a 700° F.− (372° C.−) fraction. The latter, or 700° F.− (372° C.−) fraction, can be separated into (1) a F-T Cold separator liquid, or liquid nominally boiling within a range of about $C_5$–500° F. (260° C.), and (2) a F-T hot separator liquid, or liquid nominally boiling within a range of about 500° F–700° F. (260° C.–372° C.). (3) The 700° F.+ (272° C.+) stream, with the F-T cold and hot separator liquids, constitute raw materials useful for further processing.

The F-T synthesis process is carried out at temperatures of about 160° C. to about 325° C., preferably from about 190° C. to about 260° C., pressures of about 5 atm to about 100 atm, preferably about 10–40 atm and gas hourly space velocities of from about 300 V/Hr/V to about 20,000 V/Hr/V, preferably from about 500 V/Hr/V to about 15,000 V/Hr/V. The stoichiometric ratio of hydrogen to carbon monoxide in the synthesis gas is about 2.1:1 for the production of higher hydrocarbons. However, the $H/CO_2$ ratios of 1:1 to about 4:1, preferably about 1.5:1 to about 2.5:1, more preferably about 1.8:1 to about 2.2:1 can be employed. These reaction conditions are well known and a particular set of reaction conditions can be readily determined by those skilled in the art. The reaction may be carried out in virtually any type reactor, e.g., fixed bed, moving bed, fluidized bed, slurry, bubbling bed, etc. The waxy or paraffinic products from the F-T reactor are essentially non-sulfur, non-nitrogen, non-aromatics containing hydrocarbons. This is a liquid product which can be produced and shipped from a remote area to a refinery site for further chemically reacting and upgrading to a variety of products, or produced and upgraded to a variety of products at a refinery site. For example, the hot separator and cold separator liquids, respectively, $C_4$–$C_{15}$ hydrocarbons, constitute high quality paraffin solvents which, if desired can be hydrotreated to remove olefin impurities, or employed without hydrotreating to produce a wide variety of wax products. The reactor wax, or $C_{16}$+ liquid hydrocarbons from the F-T reactor, on the other hand, can be upgraded by various hydroconversion reactions, e.g., hydrocracking, hydroisomerization, catalytic dewaxing, isodewaxing, reforming, etc. or combinations thereof, to produce (i) fuels, i.e., such as stable, environmentally benign, non-toxic mid-distillates, diesel and jet fuels, e.g., low freeze point jet fuel, high cetane jet fuel, etc., (ii) lubes, or lubricants, e.g., lube oil blending components and lube oil base stocks suitable for transportation vehicles, (iii) chemicals and specialty materials, e.g., non-toxic drilling oils suitable for use in drilling muds, technical and medicinal grade white oils, chemical raw materials, monomers, polymers, emulsions, isoparaffinic solvents, and various specialty products.

(I) Maximum Distillate

Option A

The reactor wax, or 700° F.+ (372° C.+) boiling fraction from the F-T reactor, with hydrogen, is passed directly to a hydroisomerization reactor, HI, operated at the following typical and preferred HI reaction conditions, to wit:

| HI Reactor Conditions | Typical Range | Preferred Range |
| --- | --- | --- |
| Temperature, ° F. (° C.) | 300–800 (148–427) | 550–750 (286–398) |
| Total Pressure, psig | 0–2500 | 300–1200 |
| Hydrogen Treat Rate, SCF/B | 500–5000 | 2000–4000 |

While virtually any catalyst useful in hydroisomerization or selective hydrocracking may be satisfactory for this operation, some catalysts perform better than others. For example, catalysts containing a supported Group VIII noble metal, e.g., platinum or palladium, are particularly useful as are catalysts containing one or more Group VIII base metals, e.g., nickel, cobalt, in amounts of about 0.5–20 wt %, which may or may not also include a Group VI metal, e.g., molybdenum, in amounts of about 1–20 wt %. The support for the metals can be any refractory oxide or zeolite or mixtures thereof. Preferred supports include silica, alumina, silica-alumina, silica-alumina phosphates, titania, zirconia, vanadia and other Group III, IV, VA or VI oxides, as well as Y sieves, such as ultrastable Y sieves. Preferred supports include alumina and silica-alumina where the silica concentration of the bulk support is less than about 50 wt %, preferably less than about 35 wt %.

A preferred catalyst has a surface area in the range of about 180–400 m²/gm, preferably 230–350 m²/gm, and a pore volume of 0.3 to 1.0 ml/gm, preferably 0.35 to 0.75 ml/gm, a bulk density of about 0.5–1.0 g/ml, and a side crushing strength of about 0.8 to 3.5 kg/mm.

The preferred catalysts comprise a non-noble Group VIII metal, e.g., iron, nickel, in conjunction with a Group IB metal, e.g., copper, supported on an acidic support. The support is preferably an amorphous silica-alumina where the alumina is present in amounts of less than about 30 wt %, preferably 5–30 wt %, more preferably 10–20 wt %. Also, the support may contain small amounts, e.g., 20–30 wt %, of a binder, e.g., alumina, silica, Group IVA metal oxides, and various types of clays, magnesia, etc., preferably alumina. The catalyst is prepared by coimpregnating the metals from solutions onto the support, drying at 100–150° C., and calcining in air at 200–550° C.

The preparation of amorphous silica-alumina microspheres for supports is described in Ryland, Lloyd B., Tamele, M. W., and Wilson, J. N., Cracking Catalysts, Catalysis: Volume VII, Ed. Paul H. Emmett, Reinhold Publishing Corporation, New York, 1960, pp. 5–9.

The Group VIII metal is present in amounts of about 15 wt % or less, preferably 1–12 wt %, while the Group IB metal is usually present in lesser amounts, e.g., 1:2 to about 1:20 ratio respecting the Group VIII metal. A typical catalyst is shown below:

| | |
| --- | --- |
| Ni, wt % | 2.5–3.5 |
| Cu, wt % | 0.25–0.35 |
| $Al_2O_3$—$SiO_2$ | 65–75 |
| $Al_2O_3$ (binder) | 25–30 |
| Surface Area | 290–355 m²/gm |
| Pour Volume (Hg) | 0.35–0.45 ml/gm |
| Bulk Density | 0.58–0.68 g/ml |

The 700° F.+ (372° C.+) conversion to 700° F.– (372° C.–) in the hydroisomerization unit ranges from about 20–80%, preferably 20–50%, more preferably about 30–50%. During hydroisomerization essentially all olefins and oxygen containing materials are hydrogenated.

In a preferred option, both the cold separator liquid, i.e., the $C_5$–500° (260° C.) boiling fraction, and the hot separator liquid, i.e., the 500° F.–700° F. (260° C.–372° C.) boiling fraction, are hydrotreated in a hydrotreated reactor, H/T, at hydrotreating conditions, the H/T product is combined with the HI product, and passed to a fractionator. The following describes the typical and preferred H/T reaction conditions, to wit:

| H/T Conditions | Typical Range | Preferred Range |
| --- | --- | --- |
| Temperature, ° F. (° C.) | 200–750 (94–398) | 350–600 (175–315) |
| Total Pressure, psig | 100–1500 | 300–750 |
| Hydrogen Treat Rate, SCF/B | 100–5000 | 500–1500 |

Suitable hydrotreating catalysts include those which are comprised of at least one Group VIII metal, preferably Fe, Co and Ni, more preferably Co and/or Ni, and most preferably Ni; and at least one Group VI metal, preferably Mo and W, more preferably Mo, on a high surface area support material, preferably alumina. Other suitable hydrotreating catalysts include zeolitic catalysts, as well as noble metal catalysts where the noble metal is selected from Pd and Pt. One, or more than one type of hydrotreating catalyst may be used in the same bed. The Group VIII metal is typically present in an amount ranging from about 2 to 20%, preferably from about 4 to 12%, based on the total weight of the catalyst (wt. %, dry basis). The Group VI metal will typically be present in an amount ranging from about 5 to 50 wt. %, preferably from about 10 to 40 wt. %, and more preferably from about 20 to 30 wt. %.

Gas and $C_5$–250° F. (121° C.) condensate streams are recovered from the fractionator. After separation and removal of the $C_5$–250° F. (121° C.) material, a 250° F.–700° F.– (121° C.–372° C.–) diesel fuel or diesel fuel blending component is recovered from the fractionator. A 700° F.+ (372° C.+) product component that is recovered is suitable as a lube or lube oil blending component.

The diesel material recovered from the fractionator has the properties shown below:

paraffins at least 95 wt %, preferably at least 96 wt %, more preferably at least 97 wt %, still more preferably at least 98 wt %, and most preferably at least 99 wt %. iso/normal ratio about 0.3 to 3.0, preferably 0.7–2.0; sulfur £50 ppm (wt), preferably nil; nitrogen £50 ppm (wt), preferably £20 ppm, more preferably nil; unsaturates £2 wt %; (olefins and aromatics) oxygenates about 0.001 to less than 0.3 wt % oxygen water-free basis.

The iso paraffins which are present are largely mono methyl branched, and the product contains nil cyclic paraffins, e.g., no cyclohexane.

The 700° F.– (372° C.–) fraction is rich in oxygenates, and e.g., 95% of the oxygenates, are contained in this lighter fraction. Further, the olefin concentration of the lighter fraction is sufficiently low as to make olefin recovery unnecessary; and further treatment of the fraction for olefins is avoided.

These diesel fuels generally have the properties of high cetane number, usually 50 or higher, preferably at least about 60, more preferably at least about 65, lubricity, oxidative stability, and physical properties compatible with diesel pipeline specifications.

The product can be used as a diesel fuel per se or blended with other less desirable petroleum or hydrocarbon containing feeds of about the same boiling range. When used as a blend, the product can be used in relatively minor amounts, e.g., 10% or more for significantly improving the final blended diesel product.

Although, this material will improve almost any diesel product, it is especially useful in blending with refinery diesel streams of low quality. Typical streams are raw or hydrogenated catalytic or thermally cracked distillates and gas oils.

Option B

Optionally, the cold separator liquid and hot separator liquid is not subjected to any hydrotreating. In the absence of hydrotreating of the lighter fractions, the small amount of oxygenates, primarily linear alcohols, in this fraction can be preserved, though oxygenates in the heavier reactor wax fraction are eliminated during the hydroisomerization step. Hydroisomerization serves to increase the amount of iso paraffins in the distillate fuel and helps the fuel to meet pour point and cloud point specifications, although additives may be employed for these purposes.

The oxygen compounds that are believed to promote lubricity may be described as having a hydrogen bonding energy greater than the bonding energy of hydrocarbons (the energy measurements for various compounds are available in standard references); the greater the difference, the greater the lubricity effect. The oxygen compounds also have a lipophilic end and a hydrophilic end to allow wetting of the fuel.

Preferred oxygen compounds, primarily alcohols, have a relatively long chain, i.e., $C_{12}$+, more preferably $C_{12}$–$C_{24}$ primary linear alcohols.

The amount of oxygenates present is rather small, but only a small amount of oxygenates as oxygen on a water free basis is needed to achieve the desired lubricity, i.e., at least about 0.001 wt % oxygen (water free basis), preferably 0.001–0.3 wt % oxygen (water free basis), more preferably 0.0025–0.3 wt % oxygen (water free basis).

Option C

As a further option, all or preferably a portion of the cold separator liquid can be subjected to hydrotreating while the hot separator liquid and the reactor is hydroisomerized; the wider cut hydroisomerization eliminating the fractionator vessel. However, the freeze point of the jet fuel product is compromised to some extent. Preferably, the $C_5$–350° F. (175° C.) portion of the cold separator liquid is hydrotreated, while the 350° F.+ (175° C.+) material is blended with the hot separator liquid and the reactor wax and hydroisomerized. The product of the HI reactor is then blended with the hydrotreated $C_5$–350° F. (175° C.) product and recovered.

Option D

In a fourth option, a split-feed flow scheme is provided which can produce a jet fuel capable of meeting a jet A-1 freeze point specification. In this option, the hot separator liquid and the reactor wax is hydroisomerized and the product recovered. The cold separator liquid, and optionally any residual 500° F.– (260° C.–) components after subjecting the hot separator liquid and reactor wax to treatment in a wax fractionator prior to hydroisomerization, is subjected to hydrotreating. The hydrotreated product is separated into a (a) $C_5$–350° F. (175° C.) product which is recovered, and a 350° F.+ (175° C.) product which is hydroisomerized and the hydroisomerized product then also recovered. These products can be blended together to form a jet fuel meeting a jet A-1 freeze point specification.

(II) Production of Maximum Diesel

The three streams from the F-T reactor constituting the syncrude, viz. 1) the cold separator liquid ($C_5$–500° F.), 2) hot separator liquid (500° F.–700° F.), and 3) reactor wax (700° F.+) are each treated in accordance with certain options for producing the maximum amount of a diesel fuel as follows:

Option A: (Single Reaction Vessel: Wax Hydroisomerizer)

The reactor wax from the F-T reactor is passed, with hydrogen, to a wax hydroisomerizer. The other two streams from the F-T reactor, i.e., the cold separator liquid and the hot separator liquid, are combined with the product from the hydroisomerizer, and the total mixture is passed to a fractionation column where it is separated into light gases, naphtha, and a 700° F.– (372° C.–) distillate while a 700° F.+ (372° C.+) stream is recycled to extinction in the hydroisomerizer.

The catalysts used to conduct the wax hydroisomerization reaction are described in subsection (I) Maximum Distillate, Option A.

The conditions employed for conducting the wax hydroisomerization reaction are described in subsection (I) Maximum Distillate, Option A.

Option B: (Two Vessel System: Wax Hydroisomerizer and Hydrotreater)

In this Option B, the reactor wax treating scheme described for maximum diesel in accordance with option A is unchanged, but in this instance both the cold separator liquid and hot separator liquid are hydrotreated at hydrotreating conditions, the product therefrom is then mixed with the product of the wax hydroisomerizer, and the total mixture fractionated to recover light gases, naphtha and distillate.

The hydrotreating catalyst used in conducting the hydrogenation reaction is described in subsection (I) Maximum Distillate, Option A.

The conditions employed in conducting the hydrotreating reaction is described in subsection (I) Maximum Distillate, Option A.

Option C: (One Vessel: A Wax Hydroisomerizer)

In accordance with this option, both the cold separator liquid and the reactor wax are hydroisomerized, the hot separator liquid is mixed with the product from the hydroisomerizer, and the total mixture is passed to a fractionater where it is separated into light gases, naphtha and distillate. A 700° F.+ (372° C.+) fraction is recycled to extinction in the wax hydroisomerizer.

The catalyst used to conduct the wax hydroisomerization reaction is described in subsection (I) Maximum Distillate, Option A.

The conditions employed in conducting the hydroisomerization reaction is described in subsection (I) Maximum Distillate, Option A.

(III) Production of Maximum Lube (Two reaction vessels; a Hydroisomerizer and a Catalytic Dewaxing Unit)

The reactor wax, or 700° F.+ boiling fraction, and the hot separator liquid, or 500° F.–700° F. boiling fraction, from the F-T reactor are reacted in a hydroisomerizer and the product therefrom passed to a fractionator column wherein it is split into $C_1$–$C_4$ gases, naphtha, distillate and a 700° F.+ fraction.

The 700° F.+ fraction is dewaxed, preferably in a catalytic dewaxing unit, or is both catalytically dewaxed and the product then subjected to a low vacuum distillation, or fractionation, to produce a lubricant, or lubricants. The lubricant, or lubricants, is of high viscosity index and low pour point, and is recovered in high yield.

In conducting the hydroisomerization step, the feed, at least 50 percent, more preferably at least 70 percent, of which boils above 700° F., with hydrogen, is contacted and hydroisomerized over a hydroisomerization catalyst at hydroisomerization conditions sufficient to convert from about 20 percent to about 50 percent, preferably from about 30 to about 40 percent, of the 700° F.+ hydrocarbons of the feed to 700° F.– products, based on the weight of the total feed. At these conversion levels, major amounts of the n-paraffins are hydroisomerized, or converted to isoparaffins, with minimal hydrocracking to gas and fuel by-products.

The total feed to the hydroisomerization reactor, which constitutes from about 20 percent to about 90 percent, preferably from about 30 percent to about 70 percent, by weight of the total liquid output from the F-T reactor, is fed, with hydrogen, into the hydroisomerization reactor. The hydroisomerization reactor contains a bed of hydroisomerization catalyst with which the feed and hydrogen are contacted; the catalyst comprising a metal hydrogenation or dehydrogenation component composited with an acidic oxide carrier, or support. In the hydroisomerization reactor, the feed introduced thereto is thus converted to iso-paraffins and lower molecular weight species via hydroisoomerization.

The hydrogenation or dehydrogenation metal component of the catalyst used in the hydroisomerization reactor may be any Group VIII metal of the Periodic Table of the Elements. Preferably the metal is a non-noble metal such as cobalt or nickel; with the preferred metal being cobalt. The catalytically active metal may be present in the catalyst together with one or more metal promoters or co-catalysts. The promoters may be present as metals or as metal oxides, depending upon the particular promoter. Suitable metal oxide promoters include oxides of metals from Group VI of the Periodic Table of the Elements. Preferably, the catalyst contains cobalt and molybdenum. The catalyst may also contain a hydrocracking suppressant since suppression of the cracking reaction is necessary. The hydrocracking suppressant may be either a Group IB metal or a source of sulfur, usually in the form of a sulfided catalytically active metal, or a Group IB metal and a source of sulfur.

The acidic oxide carrier component of the hydroisomerization catalyst can be furnished by a support with which the catalytic metal or metals can be composited by well known methods. The support can be any acidic oxide or mixture of oxides or zeolites or mixtures thereof. Preferred supports include silica, alumina, silica-alumina, silica-alumina-phosphates, titania, zirconia, vanadia and other Group III, IV, V or VI oxides, as well as Y sieves, such as ultra stable Y sieves. Preferred supports include alumina and silica-alumina, more preferably silica-alumina where the silica concentration of the bulk support is less than about 50 wt. %, preferably less than about 35 wt. %. Most preferably the concentration ranges from about 15 wt. % to about 30 wt. %. When alumina is used as the support, small amounts of chlorine or fluorine may be incorporated into the support to provide the acid functionality.

A preferred supported catalyst is one having surface areas in the range of about 180 to about 400 $m^2$/gm, preferably about 230 to about 350 $m^2$/gm, and a pore volume of about 0.3 to about 1.0 mL/gm, preferably about 0.35 to about 0.75 mL/gm, a bulk density of about 0.5 to about 1.0 g/mL, and a side crushing strength of about 0.8 to about 3.5 kg/mm.

The preparation of preferred amorphous silica-alumina micropheres for use as supports is described in Ryland, Lloyd B., Tamele, M. W., and Wilson, J. N., Cracking Catalysts, Catalysis; Volume VII, Ed. Paul H. Emmett, Reinhold Publishing Corporation, New York, 1960.

The hydroisomerization reactor is operated at conditions defined as follows:

| Major Operating Variables | Typical | Preferred |
|---|---|---|
| Temperature, ° C. | 200–450 | 290–400 |
| Pressure, psig | 300–10,000 | 500–1500 |
| Hydrogen Treat Rate, SCF/B | 500–5000 | 1000–4000 |

During hydroisomerization, the amount of conversion of the 700° F.+ to 700° F.– is critical, and ranges from about 20 percent to about 50 percent, preferably from about 30 to about 40 percent; and at these conditions essentially all olefins and oxygenated products are hydrogenated.

The 700° F.+ fraction from the bottom of the fractionation column is passed to a catalytic dewaxing unit wherein the waxy lubricant molecules are subjected to a pour point reducing step to produce final or near-final lubricants; some of which may require further separation in a lube vacuum pipe still. Thus, a lubricant from the catalyst dewaxing unit can be passed to a low vacuum pipe still for further concentration of lube molecules into a final product.

The final pour point reducing step in the catalyst dewaxing unit is preferably carried out by contact with a unitized mixed powder pellet catalyst comprising a dehydrogenation component, a dewaxing component, and an isomerization component. The dehydrogenation component is a catalytically active metal, or metals, comprising a Group VIB, VIIB or Group VIII metal of the Periodic Table of the Elements. The dewaxing component is comprised of an intermediate or small pore crystalline zeolite, and the isomerization component is constituted of an amorphous acidic material. Such catalyst not only produces lubricants with high viscosity indexes and significantly reduced pour points but reduced yields of undesirable gas and naphtha.

Catalytic dewaxing is a process well documented in the literature; as are catalysts useful in such processes. However, the preferred catalysts employed in the catalytic dewaxing unit are unitized mixed powder pellet catalysts characterized as particulate solids particles made by mixing together a powdered molecular sieve dewaxing component and a powdered amorphous isomerization component, one or both components of which, preferably both, contains a dehydrogenation component, or components, (or to which is subsequently added a dehydrogenation component, or components), forming a homogeneous mass from the mixture, and pelletizing the mass to produce solids particles, or pellets, each of which contains the dewaxing component, the isomerization component, and the dehydrogenation component in intimate admixture; or contains the dewaxing component and the isomerization component to which is added the dehydroisomerization component, or components, to form particulate solids wherein the dewaxing component, the isomerizing component, and hydrogenation components are present in intimate mixture. The components of the catalyst work together, cooperatively and synergistically, to selectively crack and convert the n-paraffins, or waxy components of the feed, to produce reaction products which are removed from the process as gas, while allowing branched hydrocarbons to pass downstream for removal as useful lube oil blending components, and lube oil products. This catalyst permits the conversion of Fischer-Tropsch reaction products to upgraded products from which lubricants of high viscosity index and low pour point can be recovered. This objective, and others, is achieved while minimizing the production of the less desirable gas and naphtha.

In preparation of the unitized powder pellet catalyst, the catalytic metal, or metals, dehydrogenation component can be composited with the dewaxing component, or the catalyst metal, or metals, dehydrogenation component can be composited with the isomerization component, or the catalytic metal, or metals, dehydrogenation component can be composited with both the dewaxing and the isomerization components prior to formation of the unitized powder pellet catalyst. The unitized powder pellet catalyst can also be formed from a composite of the dewaxing and isomerization components and a catalytic metal, or metals, dehydrogenation component can then be deposited thereon. Suitably, the dehydrogenation component is a Group VIB, Group VIIB, or Group VIII metal, or metals, preferably a Group VIII noble metal, or metals, of the Periodic Table of the Elements (Sargent-Welch Scientific Company: Copyright 1968), suitably ruthenium, rhodium, palladium, osmium, iridium and platinum. Suitably, the catalytic metal, or metals, dehydrogenation component is present in concentration ranging from about 0.1 percent to about 5.0 percent, preferably from about 0.1 percent to about 3.0 percent, based on the weight of the total catalyst (dry basis). In general, the molecular sieve component is present in the catalyst in concentrations ranging from about 2 percent to about 80 percent, preferably from about 20 percent to about 60 percent, based on the weight of the catalyst (dry basis). The isomerization component is generally present in concentration ranging from about 20 percent to about 75 percent, preferably from about 30 percent to about 65 percent, based on the weight of the catalyst (dry basis).

The dewaxing component of the unitized powder pellet catalyst is preferably an intermediate pore, or a small pore size molecular sieve, or zeolite. A preferred molecular sieve dewaxing component is an intermediate pore size zeolite having a 10 membered ring unidirectional pore material which has oval 1-D pores having a minor axis between 4.2 Å and 4.8 Å and a major axis between 5.4 Å and 7.0 Å as determined by X-ray crystallography.

A yet more preferred dewaxing component used to form the unitized powder pellet catalyst is characterized as a small pore molecular sieve wherein the pore windows are formed by 8 oxide atoms that form the limiting edge of this pore window. The oxide atoms each constitute one of the four oxide atoms of a tetrahedrally coordinated cluster around a silicon or aluminum ion, called a framework ion or atom. Each oxide ion is coordinated to two framework ions in these structures. The structure is referred to as "8 ring" as a shorthand way of describing a more complex structure; a shorthand notation used extensively in describing molecular sieves of this type is the *Atlas Of Zeolite Structure Types, Fourth Revised Edition* 1996 in 8 Zeolites 17:1–230, 1996. Pores of this size are such as to substantially exclude molecules of larger size than normal hexane; or, conversely, to allow entry into the pores of molecules of smaller size than normal hexane. The small pore molecular sieve is of pore size ranging between about 6.3 Å and 2.3 Å, preferably about 5.1 Å to about 3.4 Å, and comprised of a crystalline tetrahedral framework oxide component. It is preferably selected from the group consisting of zeolites, tectosilicates, tetrahedral aluminophosphates and tetrahedral silicoaluminophosphates (SAPOs). Exemplary of the molecular sieve components of this type are SAPO-56, (AFX), ZK-5 (KF1), $AlPO_4$-25 (ATV), Chabazite (CHA), TMA-E (EAB), Erionite (ERI), and Linde Type A (LTA). The Linde Type A zeolite is a particularly preferred molecular sieve.

The catalysts, besides the dewaxing, isomerization, and dehydrogenated components, may optionally also contain binder materials. Exemplary of such binder materials are silica, alumina, silica-alumina, clays, magnesia, titania, zirconia or mixtures of these with each other or with other materials. Silica and alumina are preferred, with alumina being the most preferred binder. The binder, when present, is generally present in amount ranging from about 5 percent to about 50 percent, preferably from about 20 percent to about 30 percent, based on the weight of the total catalyst (dry basis; wt. %).

The unitized catalyst can be prepared by pulverizing and powdering and then mixing together a powdered finished molecular sieve catalyst and a powdered finished isomerization catalyst, as components, and then compressing the homogeneous mass to form particulate solid shapes, e.g., lumpy solid shapes, extrudates, beads, pellets, pills, tablets or the like; each solid shape of which contains the molecular sieve dewaxing component, the isomerization component and the dehydrogenation component. One or more catalysts of given type can be pulverized and powdered, and mixed to provide a necessary component, or components, of the unitized mixed pellet catalyst. For example, a molecular sieve catalyst can supply the dewaxing and dehydrogenating functions, to wit: a molecular sieve component composited with, preferably by impregnation, a Group VIII metal, or metals, of the Periodic Table, most preferably a Group VIII noble metal, or metals, e.g., platinum or palladium. Generally, the catalyst is impregnated with from about 0.1 percent to about 5.0 percent, preferably from about 0.1 percent to about 3.0 percent, based on the weight of the catalytic component (wt. %; dry basis).

The isomerization and dehydrogenation function, on the other hand, can be supplied by an isomerization catalyst.

Thus, the isomerization component of the catalyst is comprised of an amorphous acidic material; an isomerization catalyst comprised of an acidic support composited with a catalytically active metal, preferably a Group VIII noble metal of the Periodic Table, suitably ruthenium, rhodium, palladium, osmium, iridium and platinum which can supply the isomerization and dehydrogenation functions. The isomerization catalyst component can thus be an isomerization catalyst such as those comprising a refractory metal oxide support base (e.g., alumina, silica-alumina, zirconia, titanium, etc.) on which is deposited a catalytically active metal selected from the group consisting of Group VIB, Group VIIB, Group VIII metals and mixtures thereof, preferably Group VIII metals, more preferably noble Group VIII metals, most preferably platinum or palladium and optionally including a promoter or dopant such as halogen, phosphorus, boron, yttria, magnesia, etc. preferably halogen, yttria or magnesia, most preferably fluorine. The catalytically active metals are present in the range of from about 0.1 to about 5.0 wt. %, preferably from about 0.1 to about 2.0 wt. %. The promoters and dopants are used to control the acidity of the isomerization catalyst. Thus, when the isomerization catalyst employs a base material such as alumina, acidity is imparted to the resultant catalyst by addition of a halogen, preferably fluorine. When a halogen is used, preferably fluorine, it is present in an amount in the range of about 0.1 to about 10 wt. %, preferably about 0.1 to about 3 wt. %, more preferably from about 0.1 to about 2 wt. % most preferably from about 0.5 to about 1.5 wt. %. Similarly, if silica-alumina is used as the base material, acidity can be controlled by adjusting the ratio of silica to alumina or by adding a dopant such as yttria or magnesia which reduces the acidity of the silica-alumina base material as taught in U.S. Pat. No. 5,254,518 (Soled, McVicker, Gates, Miseo). One or more isomerization catalysts can be pulverized and powdered, and mixed to provide two of the necessary components of the unitized mixed pellet catalyst.

Dewaxing is preferably carried out in the catalyst dewaxing unit in a slurry phase, or phase wherein the catalyst is dispersed throughout and movable within a liquid paraffinic hydrocarbon oil. The 700° F.+ feed is passed, with hydrogen, into the catalyst dewaxing unit and reaction carried out at catalytic dewaxing conditions tabulated as follows:

| Major Operating Variable | Typical | Preferred |
|---|---|---|
| Temperature, ° F. (° C.) | 300–840 (148–448) | 500–752 (260–400) |
| Pressure, psig | 300–10,000 | 500–1500 |
| Hydrogen Treat Rate, SCF/B | 500–5000 | 1000–4000 |

The product of the catalyst dewaxing unit is generally a fully converted dewaxed lube oil blending component, or lube oil having viscosity indexes ranging above about 110, and lube pour point below about −15° C.

The invention, and its principle of operation will be better understood by reference to the following examples with illustrate specific and preferred embodiments, and comparative data. All parts are in terms of weight except as otherwise specified.

EXAMPLE 1

Extraction of Cobalt with a Sodium salt of Ethylene Diamine Tetraacetic Acid (EDTA)

A catalyst with 22 wt % Co on silica was prepared by impregnating a particulate solids silica support twice with a solution of $Co(NO_3)_2 \cdot 6H_2O$ (50 wt % in water). Using 120 ml of solution per 30 ml support, the cobalt loading achieved after the first impregnation was less than 15 wt %. After drying/filtering the once-impregnated silica support, or precursor, was calcined for 5 hours at 250° C. to decompose the nitrate into $Co_3O_4$ to prevent redissolution of the cobalt during the second impregnation step. The second through the fourth impregnation brought the cobalt loading to 22 wt %. The precursor after each impregnation was dried and calcined at 250° C. for 5 hours.

Thirty ml of the resulting precursor was then slurried with 150 ml of a 0.001 N aqueous solution of Na-EDTA. A pink to red coloration of the solution, a characteristic of the formation of a cobalt-EDTA complex, was observed in the extraction of each of Samples 2, 3 and 4; Sample 1 was not treated with Na-EDTA. Each sample was filtered, dried and analyzed for its cobalt content as given in Table 1. Table 1 also gives the duration of the Na-EDTA extraction, illustrating the impact of the extraction time on the reduction of the cobalt loading:

TABLE 1

| Sample # | Duration of Extraction, Hours | Co wt % | Extent of Extraction, % |
|---|---|---|---|
| 1 | 0 | 22 | 0 |
| 2 | 20 | 12 | 45 |
| 3 | 90 | 10 | 55 |
| 4 | 240 | 6 | 73 |

The data show that there was a rapid initial extraction of cobalt which slowed down significantly after the first 20 minutes. This phenomenon is characteristic of a diffusion limited extraction of the cobalt present in the pores whereas the cobalt near the outside surface of the precursor particle is readily redissolved.

The several catalyst precursors listed in Table 1, were next reduced under hydrogen at 400° C. for 5 hours at 100 $hr^{-1}$ and then tested rocarbon synthesis activity. The catalytic tests were carried out in a low fixed bed unit operated: at atmospheric pressure, temperature of 190° to 195° C., GHSV=100 $h^{-1}$ and $H_2$:CO=2:1. The catalytic test sequence was carried out by increasing the temperature until the maximum yield of $C_5$+ was reached. The activities measured as CO conversion are for the optimum temperature in Table 2.

TABLE 2

| Sample # | Co % | CO conv. % | $C_5$ + Yield (g/m$^3$) |
|---|---|---|---|
| 1 | 22 | 65 | 80 |
| 2 | 12 | 68 | 110 |
| 3 | 10 | 69 | 115 |
| 4 | 6 | 72 | 120 |

The data reported in Table 2 show that higher activities and $C_5$+ selectivities are obtained following progressive Na-EDTA treatments even though a significant amount of cobalt had been extracted. For example, comparing Sample 4 with Sample 1 shows that after removal of 73 % of the cobalt originally present in the catalyst by the Na-EDTA treatment, the Na-EDTA treated catalyst is far more active (72 CO conv. % vis-a-vis 65 CO conv. %) and selective (120 $C_5+$ g/m$^3$ yield vis-a-vis 80 $C_5+$ g/m$^3$ yield) than the untreated catalyst albeit it contains only 27% as much cobalt. The duration of the extraction thus not only controls the amount of cobalt extracted, but also improves the the activity and selectivity of the extracted catalyst.

EXAMPLE 2

Extraction of Co Catalyst Precursor with EDTA/ Effect of Pore Sizes

The extraction of Co with EDTA was applied to a series of catalysts precursors with various supports, pore sizes and loadings. The extraction was carried out repeatedly slurrying the catalyst; 30 ml portions of the catalyst with 150 ml portions of a 0.001 N aqueous solution of the Na-EDTA. The supports studied included different silicas with an average pore size ranging from 11 to 52 Å and a silica-alumina with a pore size of 30 Å. The catalytic tests were carried out according to the procedure described in Example 1. Table 3 summarizes the results.

TABLE 3

| Sample # | Support | Rp(Å) | EDTA | Co % | Conversion % | $C_5 +$ (g/m$^3$) | Productivity (g/g Co.h) | (g/g Cat.h) |
|---|---|---|---|---|---|---|---|---|
| 5a | SiO$_2$ | 11 | no | 6 | 12 | 8 | — | — |
| 5b | SiO$_2$ | 11 | yes | 5 | 15 | 5 | — | — |
| 6a | SiO$_2$ | 16 | no | 14 | 50 | 60 | 0.09 | 0.013 |
| 6b | SiO$_2$ | 16 | yes | 6 | 60 | 84 | 0.28 | 0.017 |
| 1 | SiO$_2$ | 35 | no | 22 | 65 | 80 | 0.090 | 0.018 |
| 4 | SiO$_2$ | 35 | yes | 6 | 72 | 120 | 0.400 | 0.036 |
| 7a | SiO$_2$ | 52 | no | 26 | 42 | 40 | 0.04 | 0.008 |
| 7b | SiO$_2$ | 52 | yes | 7 | 36 | 21 | 0.06 | 0.004 |
| 8a | SiO$_2$/Al$_2$O$_3$ | 30 | no | 22 | 50 | 70 | 0.090 | 0.019 |
| 8b | SiO$_2$/Al$_2$O$_3$ | 30 | yes | 5 | 62 | 90 | 0.400 | 0.021 |

From these data, it is readily apparent that both the activity and productivity of the catalysts for hydrogenating carbon monoxide is generally considerably higher after treatment with the Na-EDTA than is obtained with those catalysts which were not treated with the Na-EDTA despite the fact that the former contained lesser amounts of cobalt.

EXAMPLE 3

Effect of Temperature in Conducting F-T Synthesis

Thirty ml of catalyst precursor containing 30 wt. % cobalt on silica gel was slurried with 50 ml of 0.001 N Na-EDTA solution at 100° C. while continuously slurrying for 20 minutes. The solution was then decanted, and this procedure was repeated three times giving a total extraction time of 60 minutes using a total of 150 ml of Na-EDTA solution.

Another extraction was carried out at similar conditions except that it was conducted at an extraction temperature of 20° C.

The extracted catalysts, as well as an unextracted catalyst precursor, were reduced under H$_2$ at 400° C. for 5 hours at GHSV=100 followed by Fischer-Tropsch synthesis testing at 190° C. using 2/1 H$_2$/CO gas feed at GHSV=100 and atmospheric pressure. The results, given in Table 4, clearly show that improved C$_5$+ selectivity was obtained by conducting the extraction at the more elevated temperature.

TABLE 4

| Extraction Temperature, ° C. | EDTA Treatment | Wt. % Co | % Conversion | $C_5$ + gm/m$^3$ |
|---|---|---|---|---|
| — | None | 30 | 73.8 | 88 |
| 20 | Yes | 26 | 76.4 | 89 |
| 100 | Yes | 10 | 73.8 | 115 |

The hydrocarbons produced by a hydrocarbon synthesis process according to the invention are typically upgraded to more valuable products, by subjecting all or a portion of the C$_5$+ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

Having described the invention, what is claimed is:

1. A process for the production of hydrocarbons from hydrogen and carbon monoxide comprising contacting hydrogen and carbon monoxide, at hydrocarbon synthesis reaction conditions, with a catalyst comprising a powder or particulate solids support and an oxide, or oxides of a metal, or metals; wherein the activity of the catalyst is increased by removing some of the metal atoms from said catalyst using a chelating compound having nitrogen or oxygen containing compounds and having a denticity of at least two.

2. A process according to claim 1 wherein said hydrocarbons are primarily $C_5+$ liquids.

3. A process according to claim 2 wherein at least a portion of the $C_5+$ liquids are treated by fractionation or conversion.

4. A process according to claim 3 wherein the treatment is fractionation and a transportation fuel or fuel blending product is recovered.

5. A process according to claim 4 wherein the fuel or fuel blending product is a jet or diesel fuel.

6. A process according to claim 3 wherein the treatment is conversion in the absence of a catalyst.

7. A process according to claim 6 wherein the treatment is steam cracking.

8. A process according to claim 3 wherein the treatment is conversion in the presence of a catalyst.

9. A process according to claim 8 wherein the catalytic conversion is in the presence of hydrogen.

10. A process according to claim 9 wherein the catalytic conversion is hydroisomerzation.

11. A process according to claim 10 wherein a fuel useful as transportation fuel or a blending stock therefor is recovered.

* * * * *